United States Patent [19]

Berthold et al.

[11] 4,220,799

[45] Sep. 2, 1980

[54] PROCESS FOR THE PREPARATION OF CONDENSATION PRODUCTS OF ACETOACETIC ESTERS AND ALDEHYDES

[75] Inventors: Rüdiger Berthold, Bad Soden am Taunus; Bernhard Mees, Eppstein; Hartmut Heise, Bad Soden am Taunus, all of Fed. Rep. of Germany

[73] Assignee: Hoechst Aktiengesellschaft, Frankfurt am Main, Fed. Rep. of Germany

[21] Appl. No.: 856,737

[22] Filed: Dec. 1, 1977

[30] Foreign Application Priority Data

Dec. 3, 1976 [DE] Fed. Rep. of Germany ....... 2654850

[51] Int. Cl.$^2$ ...................... C07C 69/66; C07C 69/74
[52] U.S. Cl. .................................. 560/126; 560/176; 568/346
[58] Field of Search ................ 560/126, 127, 174, 176

[56] References Cited

U.S. PATENT DOCUMENTS 2,798,793   7/1957   Moore .................................. 560/176

OTHER PUBLICATIONS

Naslund, Gunnel et al., "A New Synthesis of 1-Methyl-1-Cyclohexen-3-One and Related Compounds", Acta. Chem. Scand. 16 1329-36, (1962), See Chemical Abstracts (1963), No. 5529a.
Jones, G., "The Knoevenagel Condensation", Organic Reactions, vol. 15, chapter 2, at pp. 210 and 249, (1967-Wiley Publ.).
Fieser, Louis F. et al., "The Condensation of Nitrophenylnitromethanes With Formaldehyde", J. Am. Chem. Soc., 68 2248-9, (1946).
Hafner, von Klaus et al., "Synthesen und Reaktionen von Fulven Aldehyden", Annalen der Chemie vol. 661 (1963), 52-75.
Hann, Archie Cecil Osborn et al., "Condensation of Aldehydes With Menthyl Acetoacetate", J. Chem. Soc. 85 (1904), pp. 46-56.
Worrall, David E., "The Knoevenagel Reaction and the Synthesis of Unsaturated Nitro Compounds", J. Am. Chem. Soc. 56 (1934), pp. 1556-1558.
Naslund, Gunnel et al., "Eine neue Methode zur Darstellung von 1-Methylzyklohexe-1-on-3 und verwandten Verbindung", Acta Chem. Scand., 16 (1962), No. 6, pp. 1329-1336.

*Primary Examiner*—Natalie Trousof
*Assistant Examiner*—L. Hendriksen
*Attorney, Agent, or Firm*—Curtis, Morris & Safford

[57] ABSTRACT

The known condensation reaction of lower alkanoylacetic acid lower alkyl esters with aldehydes catalyzed by amines proceeds safe and in high yields if the amine is an aliphatic tertiary amine. The products are precursors of aromatic amines.

15 Claims, No Drawings

PROCESS FOR THE PREPARATION OF CONDENSATION PRODUCTS OF ACETOACETIC ESTERS AND ALDEHYDES

The present invention relates to a process for the preparation of condensation products of lower alkanoylacetic acid esters and aliphatic or aromatic aldehydes in the presence of amines, wherein the amine is an aliphatic tertiary amine. In Houben-Weyl, Methoden der organischen Chemie, volume VIII, pages 450 to 452 and especially 595 to 597, it has been proposed to condense aldehydes with a twofold molar quantity of $\beta$-keto-carboxylic acid esters in the presence of aliphatic secondary amines, for example diethylamine or piperidine to obtain alkylidene-bis-$\beta$-ketocarboxylic acid esters. Frequently the 1,5-diketone formed is converted spontaneously into a derivative of the cyclohexanol-3-one by intramolecular aldol condensation.

It has further been proposed (loc. cit., page 450) to use weak bases, for example ammonia, primary or secondary amines, as condensation catalysts for the Knoevenagel synthesis. These basic catalysts moreover accelerate the decarboxylation of the condensation products formed. The decarboxylation reaction may alternatively be catalyzed by tertiary aromatic bases, for example pyridine or quinoline. In said reference it has therefore been recommended to carry out the condensation especially advantageously in pyridine in the presence of a small quantity of piperidine. Pyridine and piperidine are said to have a specifically catalytic action therein. The known condensation reactions are carried out at low temperatures of about 0° C. These reaction conditions, however, are very unsuitable for batches on an industrial scale and when the reaction vessel surpasses a certain dimension, these conditions can scarcely be assured in practice owing to the disproportion between the reaction volume and the available cooling areas. When the known reactions are performed at higher temperatures, the yield of reduced considerably as a consequence of the formation of by-products. There is moreover the risk of an uncontrollable reaction which rules out operating on an industrial scale. When using pyridine as a reaction medium, said disadvantages are mitigated, but the working up of reaction mixture is extraordinarily expensive, especially owing to the fact that pyridine is water-soluble. On the other hand, when using solvents which are not miscible with water, the yields are reduced. Finally the known processes have the disadvantage that the reaction products are obtained in a solid form when working at temperatures of about 0° C. and therefore they can be discharged from the reaction vessel only with difficulty.

It has now been found that the reaction of lower alkanoylacetic acid aklyl esters and aldehydes can be carried out without the above-mentioned disadvantages when using as condensation catalyst an aliphatic tertiary amine, especially a lower trialkylamine. These catalysts according to the invention make it possible to control the reaction without difficulty and, if desired, to interrupt the reaction at the stage of the alkylidene-bis-$\beta$-keto-carboxylic acid ester. Moreover, cooling of the reaction batch, can be dispensed with. On the contrary, the reaction heat is utilized and, it desired, the reaction is completed while heating. Thus, the reaction products can be discharged in a liquid form from the reaction vessel and are allowed to crystallize in appropriate crystallization vessels.

Suitable alkanoylacetic acid alkyl esters are lower alkyl esters, in particular the methyl and ethyl esters of alkanoylacetic acids, the alkanoyl groups of which have up to 6, preferably up to 4, especially 2 or 3 carbon atoms.

Among the aliphatic aldehydes the alkanals having 1 to 10, in particular 1 to 5, carbon atoms are preferred. Preferred aromatic aldehydes are benzaldehyde as well as benzaldehydes substituted by lower alkyl, lower alkoxy, trifluoromethyl, nitro, cyano, chloro, carbamoyl, sulfamoyl, or N-(lower alkyl)-carbamoyl or sulfamoyl.

The choice of the tertiary aliphatic amine depends on the desired final product: If the final product aimed at is the alkylidene-bis-$\beta$-ketocarboxylic acid ester, an amine having lower hydroxyalkyl groups, for example triethanolamine, should be used preferably. If one wishes to obtain cyclized products, for example the corresponding cyclohexanol-3-one, and products obtained by further splitting off water and optionally by saponification and decarboxylation, from the series of the cyclohex-2-en-ones, a lower trialkylamine, especially trimethylamine or triethylamine should be used preferably. The suitable amine can be easily determined by a preliminary test, the reaction heat evolved being a measure of the activity of the catalyst. It is surprising that tertiary amines having aromatic groups, for example diethylaniline also have catalytic activity, but lead to substantially lower yields.

The reaction products are known and can be used as intermediates in a wide field of application owing to their different reactive groups. For example said cyclohexanones can be converted into their oximes, which, in turn, can be converted into the corresponding aromatic amines in known manner.

A further advantage of the amine catalysts according to the present invention resides in the fact that they catalyze a number of the known further reactions, for example splitting off of water from the cyclohexanolones, to yield cyclohexenone, as well as the saponification and decarboxylation of the carboxylic acid ester groups in $\alpha$-position to the keto group. For these further reactions, it is not required to isolate the condensation products of the first step. If the second carboxylic acid ester group, too, is to be saponified and decarboxylated, this reaction can also be performed by catalysis with acids without isolation of the previously obtained products.

The reaction conditions depend on the desired final product and on the activity of the amine catalyst. In many cases heating or cooling of the reaction batch is not required. As a general principle, however, temperatures in the range of from about $-40°$ to $120°$ C., preferably from about 0° to 80° C. and especially from about 20° to 70° C. may be applied. It is further possible to add an inert solvent or diluent, to use an excess of the alkanoylacetic acid ester or finally depending on the reaction conditions to use the amine not only in a catalytic amount, but also as a diluent, especially trialkylamines having three identical alkyl groups with up to 4 carbon atoms.

The following examples illustrate the invention and the further reactions mentioned:

EXAMPLE 1

12 g of triethylamine are added all at once to a mixture of 1740 g of acetoacetic acid methyl ester (15 mols) and 347 g of acetaldehyde (7.88 mols) at a temperature of about 20° C. The temperature rises to 60° C. within about 30 minutes. Thereafter the reaction mixture is stirred for 5 hours at 60° C. and is poured onto an enamelled plate where the crude 1,5-dimethylcyclohexan-1-ol-3-on-4,6-dicarboxylic acid dimethyl ester formed solidifies. Said ester is crushed and adherent oily products are removed by suction-filtration. There are obtained about 1800 g of crude ester, that is to say, 93% of the theory. 100 g of this crude ester is recrystallized from 110 g of methanol. Thereby the diester is obtained as pretty, white crystals having a melting point of 123° C.

EXAMPLE 2

950 g of butyrylacetic acid ethyl ester (6 mols) and 145 g of acetaldehyde (3.3 mols) are mixed while stirring and 30 g of triethylamine are added thereto. The temperature rises from 20° to 50° C. within 30 minutes. Stirring is continued for 1 hour at this temperature while heating and thereafter the mixture is kept at a temperature of 70° C. for 5 hours. The reaction mixture is cooled and allowed to crystallize in a refrigerator. After crystallization from ethanol, there is obtained pure 5-methyl-1-propyl-2-ethyl-cyclohexan-1-ol-3-on-4,6-dicarboxylic acid diethyl ester having a melting point of from 134° to 135° C.

EXAMPLE 3

12 g of triethylamine are added to a mixture of 870 g of acetoacetic acid methyl ester (7.5 mols) and 420 g of benzaldehyde (3.96 mols). The temperature rises from 25° to 32° C. within 5 minutes. After about 15 minutes, the mixture is heated to 70° C. and is stirred at this temperature for 7 hours. Next morning the batch has solidified to give a hard crystalline mass consisting of 5-phenyl-1-methyl-cyclohexan-1-ol-3-on-4,6-dicarboxylic acid dimethyl ester. The product can be recrystallized from methanol are more suitably from a mixture of methanol and methylene chloride. Melting point 89° to 90° C. The yield is about 90%.

EXAMPLE 4

20 g of triethylamine are added to a mixture of 1125 g of acetoacetic acid methyl ester (9.7 mols) and 360 g of butyraldehyde (5.0 mols). Thereby the temperatures rises from 24° to 48° C. The mixture is stirred for 4 hours without heating, then for 5 hours at 70° C. and thereafter the warm reaction product is added to 2000 g of 25% sulfuric acid. Then the mixture is heated to 130° C. for 7 hours in an autoclave. Thereafter the methanol formed is distilled off with an efficient column. The oil reaction product is separated and fractionated in vacuo. There are obtained 540 g of 1-methyl-5-propyl-cyclohexen-3-one having a melting point at 3.5 torrs of from 121° to 124° C. The yield is 73.3% of the theory.

EXAMPLE 5

25 g of triethylamine are added dropwise while stirring to a mixture of 1757 g of acetoacetic acid methyl ester (15 mols) and 570 g of 40% aqueous formaldehyde solution within 30 minutes. Thereby the temperature rises so rapidly that it is maintained at 30° C. by exterior cooling. When cooling is no longer necessary, stirring is continued for 1 hour and thereafter the mixture is heated to 70° C. and is kept at this temperature for another 2 hours. The warm condensation mixture is further treated as described in Example 4. There are obtained 368 g of 1-methyl-cyclohexen-3-one (purity 98%) which corresponds to a yield of 44% of the theory. Boiling point 91° C. at 6.0 torr.

EXAMPLE 6

There is used the batch of Example 1, which, however, is not stirred for 5 hours at 60° C. as in Example 1, but upon completion of the reaction and addition of 20 g of piperidine is heated for 5 to 6 hours to a temperature of 70° to 80° C. Thereby gas evolution occurs, which ends at the indicated period of time. Then the yellowish-brown oil formed is distilled in vacuo and after having withdrawn the first fraction, there are obtained 1170 g of 1,5-dimethyl-cyclohexen-3-on-6-carboxylic acid methyl ester. The ester is a light yellow oil having a boiling point of 120° to 125° C. at 0.5 torr. The purity (determined by gas chromatography) is 96%.

EXAMPLE 7

5 g of gaseous trimethylamine are introduced into a mixture of 1740 g of acetoacetic acid methyl ester and 347 g of acetaldehyde for a period of 5 minutes at room temperature (23° C.). After 5 minutes already, the starting reaction can be observed by the temperature increase. After 45 minutes, the temperature maximum of about 60° C. is attained and the reaction is continued until completion by heating to 70° C. After 5 hours, the reaction mixture is cooled. The 1,5-dimethyl-cyclohexan-1-ol-3-on-4,6-dicarboxylic acid dimethyl ester crystallizes over-night. It is worked up as in Example 1.

When using tripropylamine or tributylamine, the reaction takes place in an analogous manner.

EXAMPLE 8

Into a 3 liter flanged beaker there are added 347 g of acetaldehyde to 1759 g of acetoacetic acid methyl ester and then 18 g (=0.12 mol) of triethanolamine are added at an internal temperature of 20° C. The temperature rises to 25° C. within 1 hour and thereafter begins to drop again. Then the reaction mixture is heated to 70° C. and is stirred overnight at this temperature. The batch does not solidify overnight. There is formed a yellow oil, 85 to 90% of which consist of ethylidene-bis-acetoacetic acid ester, 7 to 10% consist of acetoacetic acid methyl ester and only 3 to 5% consist of 1,5-dimethylcyclohexan-1-ol-3-on-4,6-dicarboxylic acid dimethyl ester as could be demonstrated by the NMR spectrum.

When using N-methyl-diethanolamine the internal temperature rises from 20° to 55° C. within 82 minutes under the same reaction conditions and the batch begins to solidify only after 2 days.

When using N,N-dimethylethanolamine, the temperature rises from 20° to 60° C. within 30 minutes and the batch solidifies already after 10 hours to give 1,5-dimethylcyclohexan-1-ol-3-on-4,6-dicarboxylic acid dimethyl ester.

We claim:
1. A process for making a condensation product selected from bis-β-ketocarboxylic acid esters and cyclic ketones which comprises reacting a lower alkanoylacetic acid lower alkyl ester with an alkanal of 1 to 10 carbon atoms at a temperature of −40° to 120° C. in the presence of a catalyst which is a lower hydroxyalkyl tertiary amine.

2. A process as claimed in claim 1, wherein the aldehyde is an alkanal of 1 to 10 carbon atoms, benzaldehyde or a benzaldehyde substituted by lower alkyl, lower alkoxy, trifluoromethyl, nitro, cyano, chlorine, carbamoyl, sulfamoyl, carbamoyl substituted at the nitrogen by lower alkyl or sulfamoyl substituted at the nitrogen by lower alkyl.

3. A process as claimed in claim 1, wherein the reaction is performed at 0° to 80° C.

4. A process as claimed in claim 1, wherein the reaction is performed at 20° to 70° C.

5. A process as claimed in claim 1, wherein the reaction is performed in an inert solvent or diluent.

6. A process as claimed in claim 1, wherein an excess of said ester serves as a solvent or diluent.

7. A process as claimed in claim 1, wherein an excess of said amine serves as a solvent or diluent.

8. A process according to claim 1 wherein said alkanal is formaldehyde.

9. A process according to claim 1 wherein said alkanal is acetaldehyde.

10. A process according to claim 1 wherein said alkanal is butyraldehyde.

11. A process according to claim 1 wherein said amine is triethanolamine.

12. A process according to claim 1 wherein said amine is N-methyl-diethanolamine.

13. A process according to claim 1 wherein said amine is N,N-dimethyl-ethanolamine.

14. A process for making a bis-β-ketocarboxylic acid ester which comprises reacting a lower alkanoylacetic acid lower alkyl ester with an alkanal of 1 to 10 carbon atoms at a temperature of −40° to 120° C. in the presence of a catalyst which is triethanolamine.

15. A process for making a cycloketone which comprises reacting a lower alkanoylacetic acid lower alkyl ester with an alkanal of 1 to 10 carbon atoms at a temperature of −40° to 120° C. in the presence of a catalyst which is dimethylmonoethanolamine.

* * * * *